United States Patent
Dees, Jr. et al.

(10) Patent No.: US 11,622,814 B2
(45) Date of Patent: Apr. 11, 2023

(54) INTRAOPERATIVE IMPLANT AUGMENTATION

(71) Applicant: Smith & Nephew, Inc., Memphis, TN (US)

(72) Inventors: Roger Ryan Dees, Jr., Drummonds, TN (US); Sied W. Janna, Memphis, TN (US); Daniel Farley, Memphis, TN (US); Branislav Jaramaz, Pittsburgh, PA (US)

(73) Assignee: Smith & Nephew, Inc., Memphis, TN (US)

( * ) Notice: Subject to any disclaimer, the term of this patent is extended or adjusted under 35 U.S.C. 154(b) by 505 days.

(21) Appl. No.: 16/642,612

(22) PCT Filed: Aug. 30, 2018

(86) PCT No.: PCT/US2018/048852
§ 371 (c)(1),
(2) Date: Feb. 27, 2020

(87) PCT Pub. No.: WO2019/046579
PCT Pub. Date: Mar. 7, 2019

(65) Prior Publication Data
US 2020/0197103 A1    Jun. 25, 2020

Related U.S. Application Data

(60) Provisional application No. 62/552,645, filed on Aug. 31, 2017.

(51) Int. Cl.
*A61B 34/20* (2016.01)
*A61B 34/10* (2016.01)
(Continued)

(52) U.S. Cl.
CPC ............ *A61B 34/20* (2016.02); *A61B 34/10* (2016.02); *A61B 34/25* (2016.02);
(Continued)

(58) Field of Classification Search
CPC ............ A61B 34/20; A61B 2034/108; A61B 2034/2055; A61B 2034/2068; A61F 2/30734; A61F 2002/30736
See application file for complete search history.

(56) References Cited

U.S. PATENT DOCUMENTS 5,769,078 A * 6/1998 Kliegis ................. A61B 34/70
600/407
2003/0208296 A1* 11/2003 Brisson ................. A61B 90/10
700/117

(Continued)

FOREIGN PATENT DOCUMENTS

| AU | 2011293202 A1 * | 4/2013 | ............. A61K 35/32 |
| AU | 2012362279 A2 * | 8/2014 | ............. A61B 17/164 |
| AU | 2013397940 A1 * | 3/2016 | ............. A61F 2/34 |
| WO | 2016086049 A1 | 6/2016 | |

OTHER PUBLICATIONS

International Search Report and Written Opinion for PCT/US2018/048852 dated Dec. 17, 2018.

*Primary Examiner* — Anu Ramana
(74) *Attorney, Agent, or Firm* — DLA Piper LLP (57) ABSTRACT

Methods and systems of augmenting an implant intraoperatively and preparing a cone for revision surgical procedure are disclosed. A system includes a cutting device, a tracking and navigation system and a cutting system in operable communication with the cutting device and the tracking and navigation system. The cutting device includes a communication system, a cutting element, and a plurality of optical trackers. The tracking and navigation system is configured to detect a location of optical trackers. The control system is configured to cause the tracking and navigation system to (Continued)

detect the location of the cutting device, determine a revised shape for an implant cavity, cause the cutting device to cut the implant cavity to the revised shape, select a shape for a cone to be placed in the revised implant cavity, and machine the cone to the selected shape.

25 Claims, 6 Drawing Sheets

(51) Int. Cl.
  *A61B 34/00* (2016.01)
  *A61F 2/30* (2006.01)
(52) U.S. Cl.
  CPC .... *A61F 2/30942* (2013.01); *A61B 2034/104* (2016.02); *A61B 2034/108* (2016.02); *A61B 2034/2051* (2016.02); *A61B 2034/2055* (2016.02); *A61B 2034/2068* (2016.02); *A61F 2002/3096* (2013.01); *A61F 2002/30217* (2013.01); *A61F 2002/30736* (2013.01)

(56) References Cited

U.S. PATENT DOCUMENTS

| | | |
|---|---|---|
| 2011/0208256 A1 | 8/2011 | Zuhars |
| 2016/0338776 A1 | 11/2016 | Jaramaz et al. |
| 2016/0342766 A1 | 11/2016 | Darwood |

\* cited by examiner

INTRAOPERATIVE IMPLANT AUGMENTATION

CLAIM OF PRIORITY

This patent application is a national stage application of PCT Application No. PCT/US2018/048852, titled "Intraoperative Implant Augmentation," filed on Aug. 30, 2018, which claims the benefit of priority of U.S. Provisional Patent Application Ser. No. 62/552,645, titled "Intraoperative Implant Augmentation," filed on Aug. 31, 2017, each of which is hereby incorporated by reference herein in its entirety.

TECHNICAL FIELD

The present disclosure generally relates to implant revision surgery. More specifically, the present disclosure relates to intraoperative augmentation of cones for patient-specific revision knee replacement surgery.

BACKGROUND

The use of computers, robotics, and imaging to provide aid during surgery is known in the art. There has been a great deal of study and development of computer-aided navigation and robotic systems used to guide surgical procedures. For example, a precision freehand sculptor employs a robotic surgery system to assist the surgeon in accurately cutting a bone into a desired shape. In procedures such as total knee arthroplasty (TKA), computer-aided surgery techniques have been used to improve the accuracy and reliability of the surgery.

In a typical arthroscopic procedure, a practitioner can use a navigation system, such as an optical or electromagnetic tracking system, for additional guidance so that any cuts or bone shape alterations that are made are consistent with a registered surgical plan. Both types of tracking systems use sensors that are attached to both the bone to be resected and the cutting instrument to be used by the surgeon. For example, during TKA, a tracking device can be attached to the patient's femur, the patient's tibia, and one or more surgical tools such as a handheld rotary cutting device. The navigation system can register an initial location of the tracking devices in the surgical space and track the position of the patient and the surgical tool(s) throughout the surgical procedure.

Following a joint replacement surgery, bone defects associated with implant component loosening, subsidence, and osteolysis can occur, requiring a revision surgery to correct or remedy the bone defects. Typically, the bone defects involve significant bone loss of either the proximal tibia or the distal femur.

Reconstruction techniques typically include inserting a cone, or similar augment, into the defected area. In order to correct the defect, a surgeon can select an appropriately sized cone, smooth out the defected area using a cutting burr attachment on a rotary cutting device, and insert the cone into the smoothed area for a test fit. Depending upon the test fit, the surgeon can remove more material or select a different sized cone. Once the surgeon is satisfied with the fit, the surgeon can permanently insert the cone and continue the revision surgery.

During such a reconstruction procedure, the fit of the cone is important to prevent additional bone loss. For example, if the cone does not provide some level of pressure against an adjacent bone surface, that adjacent bone surface may deteriorate over time. Thus, it is important that the surgeon precisely smooth out the defected area, and ensure a tight fit between the cone and the smoothed bone. Additionally, achieving good stability in the implanted joint can require a good fit (e.g., >60% contact) between the fitted cone and the surrounding bone. However, such an intraoperative reconstruction process can be burdensome and time-consuming as the surgeon strives for a good fit between the cone and the surrounding bone.

SUMMARY

This summary is submitted with the understanding that it will not be used to interpret or limit the scope or meaning of the present disclosure.

A method of augmenting an implant intraoperatively is provided. The method includes removing an existing implant from an implant cavity, determining a shape of the implant cavity, selecting a shape and position for a cone based on at least the determined shape of the implant cavity, machining the cone having the selected shape, installing the cone at the selected position within the implant cavity, and installing a revision implant in the cone. According to certain embodiments, the method further includes defining a coordinate system for a tracking and navigation system during a surgical procedure. In some embodiments, defining the coordinate system includes identifying a set of fiduciary points on a patient using a registered probe having a plurality of optical trackers.

According to certain embodiments, determining the shape of the implant cavity comprises tracing a surface of the implant cavity using a registered probe having a plurality of optical trackers. According to certain embodiments, determining the shape of the implant cavity comprises tracking a location of a cutting device used to shape the surface of the implant cavity.

According to certain embodiments, the method further includes simulating the shape and position of the cone using a graphical user interface. In some embodiments, selecting the shape and position of the cone includes modifying one or more of the shape of the cone and the position of the cone within the graphical user interface, and altering the selected shape and position of the cone based on the modifications.

According to certain embodiments, the method further includes creating a set of instructions for machining the cone. In some embodiments, machining the cone comprises machining the cone intraoperatively.

According to certain embodiments, the method further includes updating the shape of the cone from the selected shape to a revised shape, and machining the machined cone to the revised shape.

A method of preparing a custom cone for a revision surgical procedure is also provided. The method includes providing a cone blank having a standardized size and shape on a shaping fixture, determining, by a tracking and navigation system, outer dimensions for the cone blank based on the standardized size and shape of the cone blank and one or more registration features of the shaping fixture, determining, by the tracking and navigation system, a position of a cutting device, and providing one or more operational instructions to the cutting device to shape the cone blank to the custom cone. In some embodiments, the method further includes registering the one or more registration features on the shaping fixture by identifying a set of fiduciary points on the shaping fixture using a registered probe having a plurality of optical trackers.

According to certain embodiments, providing one or more operational instructions comprises controlling, by a control system in operable communication with the tracking and navigation system, operation of the cutting device based on the position of the cutting device and the custom cone shape. In some embodiments, controlling operation of the cutting device comprises wirelessly controlling operation of the cutting device.

According to certain embodiments, the cutting device is a handheld cutting device. According to certain embodiments, the cutting device comprises a plurality of optical trackers.

In addition, a method of preparing a custom cone for a revision surgical procedure is provided. The method includes providing a cone blank having a standardized size and shape on a shaping fixture, determining a minimum cone volume for the custom cone, determining, by a tracking and navigation system, a location of the cone blank, determining, by the tracking and navigation system, a location of a cutting device, wherein the cutting device comprises a cutting element, and causing the cutting device to operate the cutting element when the cutting element of the cutting device is located within removable cone material surrounding the minimum cone volume of the cone blank.

According to certain embodiments, determining a minimum cone volume for the custom cone comprises generating a three-dimensional model of the cone blank comprising the minimum cone volume surrounded by the removable cone material.

According to certain embodiments, determining a minimum cone volume comprises determining a shape of an implant cavity, and selecting a shape and position for the minimum cone value based on at least the determined shape of the implant cavity.

According to certain embodiments, determining a location of the cone blank comprises registering one or more registration features on the shaping fixture by identifying a set of fiduciary points on the shaping fixture using a registered probe having a plurality of optical trackers.

According to certain embodiments, determining a location of a cutting device comprises identifying a location of each of a plurality of optical trackers associated with the cutting device.

A system for augmenting an implant intraoperatively is provided. The system includes a cutting device, a tracking and navigation system, and a control system. The cutting device includes a communication system, a cutting element, and a plurality of optical trackers. The tracking and navigation system is configured to detect a location of one or more optical trackers. The control system is in operable communication with the tracking and navigation system and the cutting device. The control system is configured to cause the tracking and navigation system to detect a location of the cutting device by identifying a location of the plurality of optical trackers associated with the cutting device, determine a revised shape for the implant cavity, cause the cutting device to cut the implant cavity to the revised shape when the tracking and navigation system identifies that the cutting element is positioned within the implant cavity, select a shape for a cone based on at least the determined shape of the implant cavity, and cause the cutting device to machine a cone blank to the selected shape when the tracking and navigation system identifies that the cutting element is positioned in proximity to the cone blank.

According to certain embodiments, the communication system of the cutting device comprises a wireless communication system. According to certain embodiments, the cutting element of the cutting device comprises a rotary burr.

According to certain embodiments, the system may further include a probe and a shaping fixture. The probe includes a plurality of optical trackers. The shaping fixture includes a plurality of registration points. In such an embodiment, the control system is further configured to determine a location of the shaping fixture by directing a user to place the probe on each of the plurality of registration points, and for each registration point, causing the tracking and navigation system to detect a location of the plurality of optical trackers associated with the probe.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the present disclosure. In the drawings.

DETAILED DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

For the purposes of the present disclosure, the term "implant" is used to refer to a prosthetic device or structure manufactured to replace or enhance a biological structure, either permanently or on a trial basis. For example, in a knee replacement procedure, an implant can be placed on one or both of the tibia and femur. While the term "implant" is generally considered to denote a man-made structure (as contrasted with a transplant), for the purposes of this specification, an implant can include a biological tissue or material transplanted to replace or enhance a biological structure.

Similarly, as used herein, the term "cone" refers to a cone, sleeve, or other similar augment used during revision surgery for establishing a stable construct for an implant component during the procedure. A cone is constructed, at least in part, from a surgically safe and stable material such as porous tantalum, porous titanium, and/or titanium alloys, and is typically sized and shaped to counteract various bone defects that are traditionally encountered during joint revision surgery. In certain implementations, the cones can have a coating such as hydroxylapatite to promote bone growth.

The embodiments of the present teachings described below are not intended to be exhaustive or to limit the teachings to the precise forms disclosed in the following detailed description. Rather, the embodiments are chosen and described so that others skilled in the art may appreciate and understand the principles and practices of the present teachings.

This disclosure describes intraoperative alteration of cones, and similar augments, for patient-specific knee revision surgery. During the surgical procedure, the cone can be altered based upon feedback provided from a computer-aided robotic surgical system. For example, a tracking and navigation system associated with the computer-aided robotic surgical system can be configured to map the surface of a patient's bone. In particular, during a revision surgery, the surgeon can be instructed to paint the surface of a defected area, for example, within an existing implant cavity, by tracing or otherwise moving the tip of a tracked surgical probe around the surface of the defected bone. The tracking system can then create a virtual mapping of the defected bone surface.

From this virtual mapping, in combination with previously identified anatomical landmarks, the surgical system can determine an optimal cone shape for the defected area. Additionally or alternatively, the surgical system can also provide the surgeon with instructions to resect a specific portion of the bone in the defected area. Based upon this optimal cone shape, the surgical system can generate a set of instructions for forming a patient-specific custom cone. These instructions can be performed by the surgeon using a handheld cutting device, or by a standalone cutting or milling device such as a lathe, mill, computer numerical controlled (CNC) machine, or other similar cutting or milling devices. Similarly, the cone can be manufactured from a surgically safe material using three-dimensional (3D) printing techniques.

The disclosed tracking system as described above is particularly adapted for surgical procedures that utilize surgical navigation systems, such as the NAVIO® surgical navigation system. Such procedures can include knee replacement revision surgery. NAVIO is a registered trademark of BLUE BELT TECHNOLOGIES, INC. of Pittsburgh, Pa.

The NAVIO® surgical navigation system can be implemented as a robotically assisted surgical navigation system that is capable of tracking flexion and extension of a joint for a particular patient. The system can provide feedback on joint alignment to aid in joint balancing. In various embodiments, the system can use a series of passive optical trackers to monitor and track a patient during a joint replacement procedure. For example, during TKA, optical trackers can be secured to the femur and tibia to track the motion of the knee. A hand-held probe can be used to define the approximate shape of the tibio-femoral articulating surfaces by, as noted above, painting the surfaces by defining a number of points on the surface by dragging or otherwise moving the probe around the surface.

Figure 1:
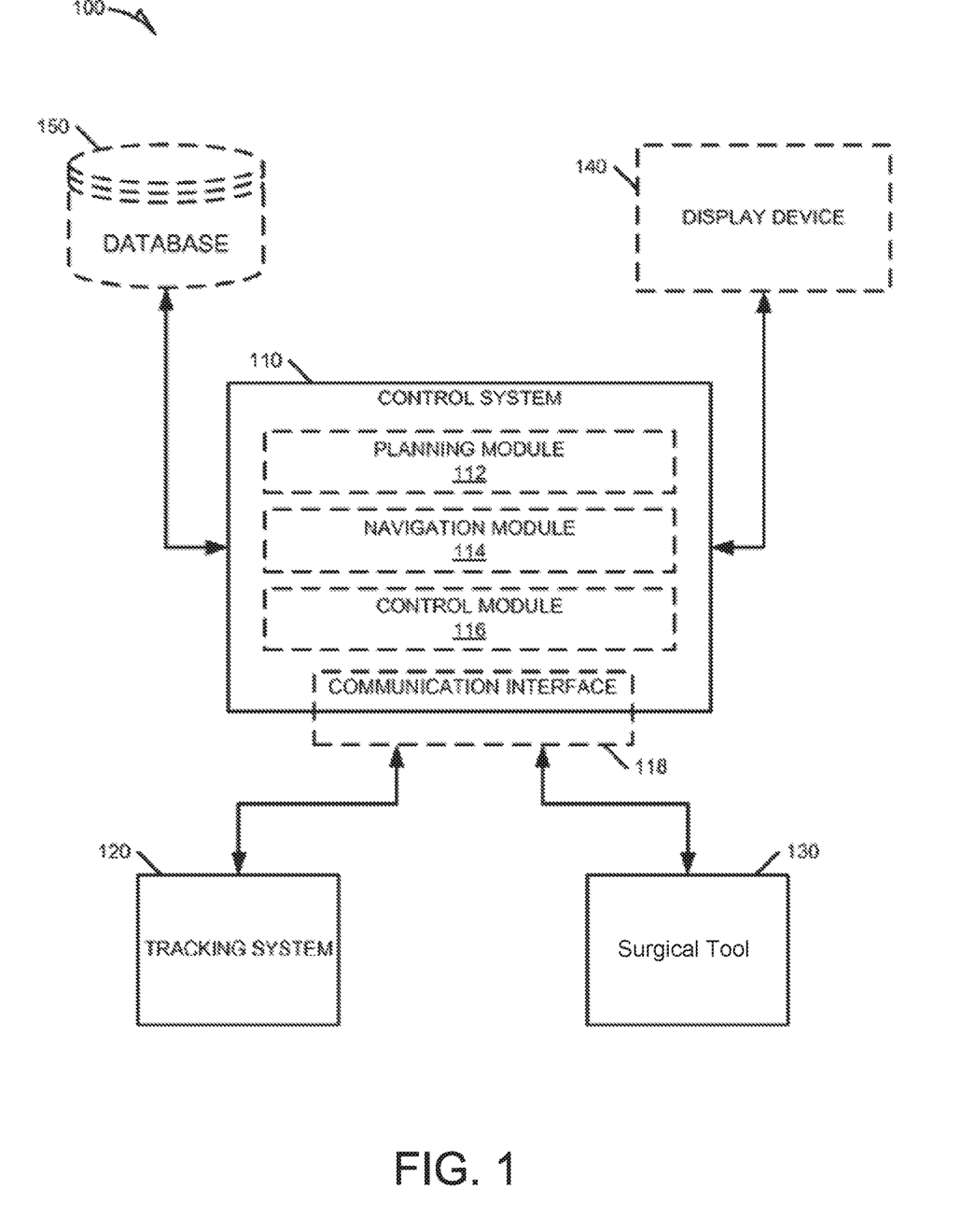
FIG. 1 depicts a block diagram illustrating a system for providing navigation and control to a surgical tool in accordance with an embodiment.

FIG. 1 is a block diagram depicting a system 100 for providing navigation and control to a surgical tool 130 according to an example embodiment. For example, the system 100 can include a control system 110, a tracking system 120, and a surgical tool 130. In some embodiments, the system 100 may further include a display device 140 and a database 150. In an example, these components can be combined to provide navigation and control of the surgical tool 130 during an orthopedic (or similar) prosthetic implant surgery.

The control system 110 can include one or more computing devices configured to coordinate information received from the tracking system 120 and provide control to the surgical tool 130. In an example, the control system 110 can include a planning module 112, a navigation module 114, a control module 116, and a communication interface 118. The planning module 112 can provide pre-operative planning services that enable clinicians to plan a procedure virtually prior to entering the operating room. The background discusses a variety of pre-operative planning procedures used in total knee replacement that can be used in surgical robotic assisted joint replacement procedures.

In an example, such as TKA, the planning module 112 can be used to manipulate a virtual model of the implant in reference to a virtual implant host model. The implant host model can be constructed from actual scans of the target patient, such as computed tomography (CT), magnetic resonance imaging (MRI), positron emission tomographic (PET), or ultrasound scanning of the joint and surrounding structure. Alternatively, pre-operative planning can be performed by selecting a predefined implant host model from a group of models based on patient measurements or other clinician-selected inputs. In certain examples, pre-operative planning is refined intra-operatively by measuring the patient's (target implant host's) actual anatomy. In an example, a point probe connected to the tracking system 120 can be used to measure the target implant host's actual anatomy.

In an example, the navigation module 114 can coordinate tracking the location and orientation of the implant, the implant host, and the surgical tool 130. In certain examples, the navigation module 114 can also coordinate tracking of the virtual models used during pre-operative planning within the planning module 112. Tracking the virtual models can include operations such as alignment of the virtual models with the implant host through data obtained via the tracking system 120. In these examples, the navigation module 114 receives input from the tracking system 120 regarding the physical location and orientation of the surgical tool 130 and an implant host. Tracking of the implant host can include tracking multiple individual bone structures. For example, the tracking system 120 can individually track the femur and the tibia during a TKA procedure using tracking devices anchored to the individual bones.

In an example, the control module 116 can process information provided by the navigation module 114 to generate control signals for controlling the surgical tool 130. In certain examples, the control module 116 can also work with the navigation module 114 to produce visual animations to assist the surgeon during an operative procedure. Visual animations can be displayed via a display device, such as display device 140. In an example, the visual animations can include real-time 3-D representations of the implant, the implant host, and the surgical tool 130, among other things. In certain examples, the visual animations are color-coded to further assist the surgeon with positioning and orientation of the implant.

In an example, the communication interface 118 facilitates communication between the control system 110 and external systems and devices. The communication interface 118 can include both wired and wireless communication interfaces, such as Ethernet, IEEE 802.11 wireless, or Bluetooth, among others. As illustrated in FIG. 1, in this example, the primary external systems connected via the communication interface 118 include the tracking system 120 and the surgical tool 130. Although not shown, the database 150 and the display device 140, among other devices, can also be connected to the control system 110 via the communication interface 118. In an example, the communication interface 118 communicates over an internal bus to other modules and hardware systems within the control system 110.

In an example, the tracking system 120 provides location and orientation information for surgical devices and parts of an implant host's anatomy to assist in navigation and control of semi-active robotic surgical devices. The tracking system 120 can include a tracker that includes or otherwise provides tracking data based on at least three positions and at least three angles. The tracker can include one or more first tracking markers associated with the implant host and one or more second markers associated with the surgical device (e.g., surgical tool 130). The markers or some of the markers can be one or more of infrared sources, Radio Frequency (RF) sources, ultrasound sources, and/or transmitters. The tracking system 120 can thus be an infrared tracking system, an optical tracking system, an ultrasound tracking system, an inertial tracking system, a wired system, and/or a RF tracking system. One illustrative tracking system can be the OPTOTRAK® 3-D motion and position measurement and tracking system described herein, although those of ordinary skill in the art will recognize that other tracking systems of other accuracies and/or resolutions can be used. OPTOTRAK is a registered trademark of NORTHERN DIGITAL INC. of Waterloo, Ontario, Canada.

Figure 2:
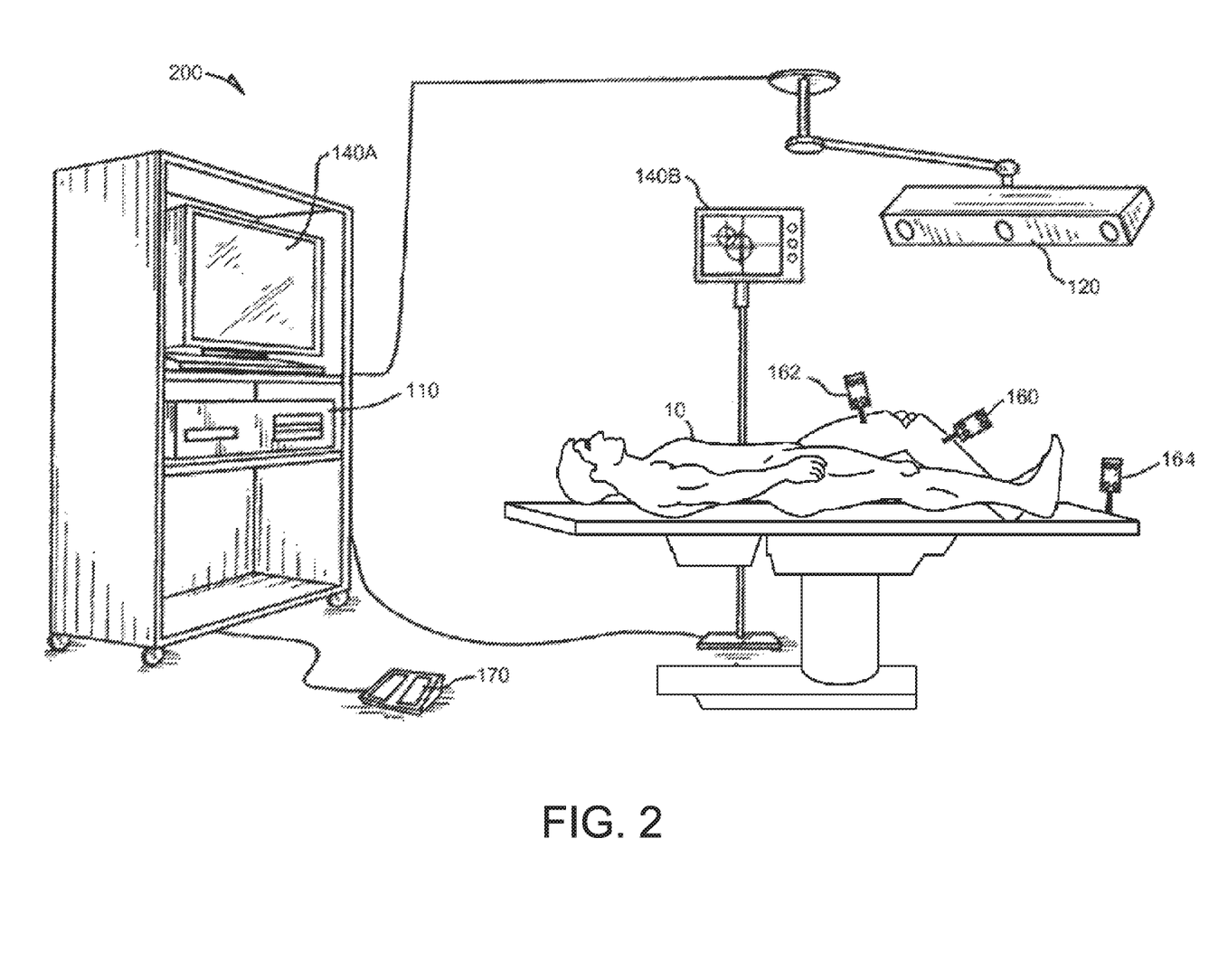
FIG. 2 depicts a diagram illustrating an environment for operating a system for navigation and control during a surgical procedure in accordance with an embodiment.

FIG. 2 is a diagram illustrating an environment for operating a system 200 for navigation and control of surgical tool (e.g., surgical tool 130 as described in regard to FIG. 1), according to an example embodiment. In an example, the system 200 can include components similar to those discussed above in reference to system 100. For example, the system 200 can include a control system 110, a tracking system 120, and one or more display devices, such as display devices 140A and 140B. The system 200 also illustrates an implant host 10, tracking markers 160, 162, and 164, and a foot control 170.

In an example, the tracking markers 160, 162, and 164 can be used by the tracking system 120 to track location and orientation of the implant host 10, one or more surgical tools (including, for example, similar tracking markers), and a reference, such as an operating table (tracking marker 164). In this example, the tracking system 120 uses optical tracking to monitor the location and orientation of tracking markers 160, 162, and 164. Each of the tracking markers 160, 162, and 164 includes three or more tracking spheres that provide easily processed targets to determine location and orientation in up to six degrees of freedom. The tracking system 120 can be calibrated to provide a localized 3-D coordinate system within which the implant host 10 and one or more surgical tools can be spatially tracked. For example, as long as the tracking system 120 can image three of the tracking spheres on a tracking marker, such as tracking marker 160, the tracking system 120 can utilize image processing algorithms to generate points within the 3-D coordinate system. Subsequently, the tracking system 120 (or the navigation module 114 (FIG. 1) within the control system 110) can use the 3 points to triangulate an accurate 3-D position and orientation associated with the item to which the tracking marker is affixed, such as the implant host 10 or a surgical tool. Once the precise location and orientation of the surgical tool is known, the system 200 can use the known properties of the surgical tool to accurately calculate a position and orientation of the surgical tool relative to the implant host 10.

As noted above, during a joint revision surgery, a cone can be inserted into a cavity to correct for any bone defects. The cones can be used to reinforce a cortical bone, fill voids that result from removal of existing implant components, and/or provide adequate support to the tibial plate or femoral implant. Existing techniques include sequential removal of bone material and test fitting the cone. Final cone placement is achieved by impaction. However, traditional bone preparation often leaves gaps and voids that are filled with graft material. Using the techniques taught herein, a surgeon can accurately map the implant cavity to be filled by a cone and create a custom cone that is patient specific. Rather than use a standard sized and shaped cone (which requires precise shaping of the implant cavity by the surgeon), the custom cone as taught herein provides a highly accurate and tight fit (e.g., greater than 75% contact between the cone and the existing bone) within the implant cavity, thereby increasing the stability of the joint after the revision surgery. There are numerous benefits to providing a more accurate and tight fit. For example, existing bone has an established blood supply when compared to grafted bone, which includes the risk of non-union with the existing bone. Additionally, existing bone improves initial stability and fixation for the revision implant.

Figure 3:
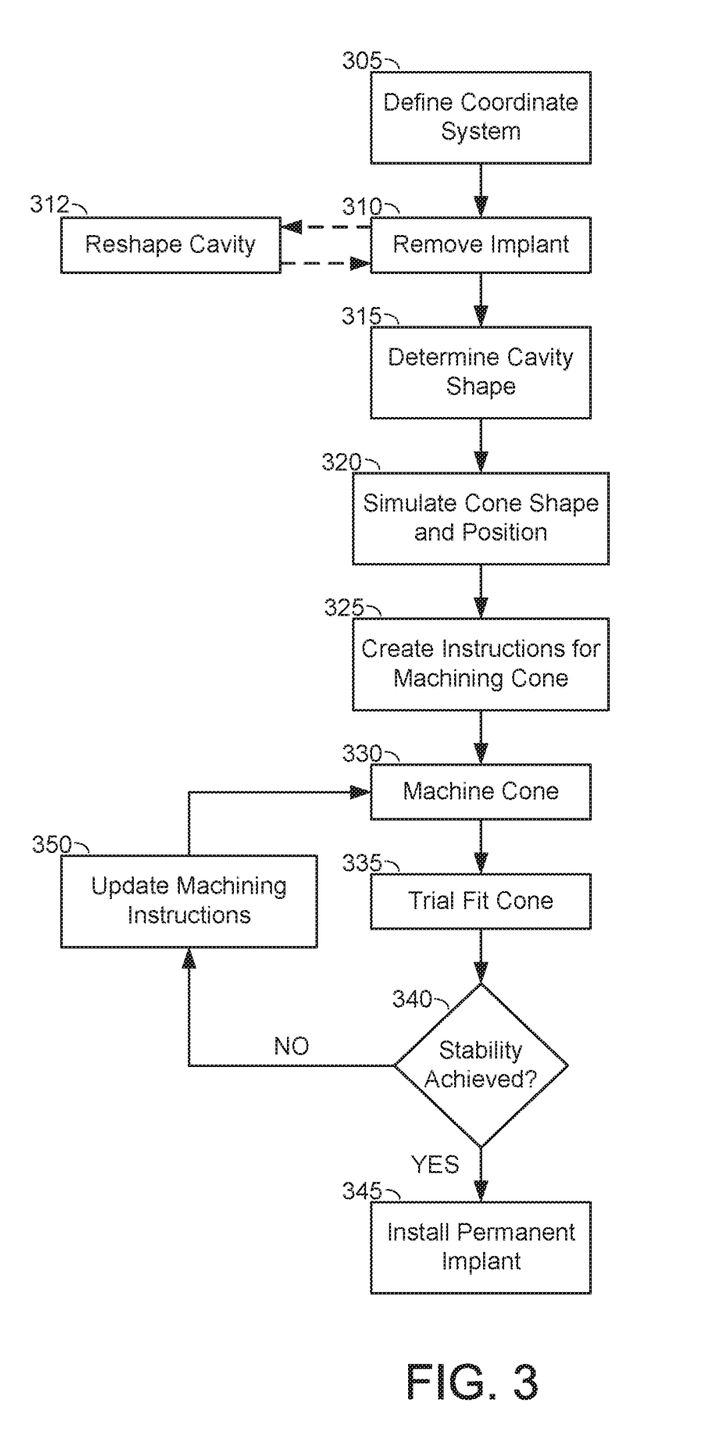
FIG. 3 depicts a sample flow diagram of a joint revision surgery including creating a patient-specific augmentation cone in accordance with an embodiment.

FIG. 3 illustrates a sample process for creating a custom cone during a knee revision surgery. It should be noted that, for discussion purposes, knee replacement revision procedures are described herein by way of example only. The techniques described herein can be applied to any joint implant revision procedure.

In certain implementations, during surgery with a computer-aided robotic surgical system such as those described herein, the surgeon can be guided through the procedure by a touchscreen monitor operably connected to the surgical system. The monitor can display a bone model representing, for example, the patient's femur and tibia, the varus/valgus deformity, the position of tracked instruments, as well as other information related to the surgical procedure.

As shown in FIG. 3, the surgical system can define 305 a coordinate system for the tracking and navigation system during the knee revision surgery. As noted above, a surgeon can attach optical trackers to various positions on the patient, such as the patient's femur and tibia, during a surgical procedure. The surgeon can use a registered probe (e.g., a probe having a size and shape known to the tracking system) having a set of attached or integrated optical trackers to identify a set of fiduciary points on the patient. The tracking system can use the optical markers on the probe, the optical markers on the patient, and the location of the fiduciary points to define 305 the coordinate system and the various optical markers within the coordinate system. Once defined 305, the tracking system can accurately track any optical markers as they pass through the coordinate system, whether attached to the patient or to a surgical tool being used during the procedure.

The surgeon can then remove 310 the existing implant. In order to remove 310 the implant, the surgeon can cut or remove various soft tissue to provide access to the existing implant. Upon removal 310 of the implant, the surgeon can evaluate the implant cavity and, if necessary, use a cutting tool, such as a handheld rotary device with a cutting burr, to reshape 312 the cavity.

In certain procedures, a two-stage knee revision is performed. For example, if a knee undergoing revision surgery includes a large area of infection, the existing implant can be removed and replaced with an interim device such as a cement spacer or temporary arthrodesis) while treating the infection in the first stage. The second stage can be performed several weeks later (depending upon the eradication of the infection). In the second stage, the interim device can be removed 310, and the process continues as shown in FIG. 3.

After removal 310, the surgeon can then use the probe or another tracked tool to trace the surface of the implant cavity. By monitoring the position and orientation of the probe as the surgeon traces the cavity surface, the surgical system can determine 315 the shape of the implant cavity. For example, as the surgeon is tracing the surface of the implant cavity, the tracking system can continually monitor the position and orientation of the probe and record the position of the probe's tip. Once the tracking system has a sufficient amount of position information, the surgical system can receive the position information from the tracking system and use the position information to map or model the surface of the cavity. From the mapped or modeled surface information, the surgical system can determine 315 the cavity shape by identifying the negative space defined within the surface information.

In certain implementations, the surgical system can map the cavity geometry by tracking the burr during resection. For example, as a surgeon is using a burr to shape the cavity, the tracking system can track the rotary tool and, by extension, track the burr to map the geometry of the cavity. Generating models related to bone shape and cavities during resection is further described in U.S. patent application Ser. No. 14/955,742 entitled "Systems and Methods for Planning and Performing Image Free Implant Revision Surgery," the content of which is incorporated herein by reference.

The surgical system can further simulate 320 a custom cone shape and position by identifying the negative space defined within the surface information. However, in certain implementations, the custom cone shape and position may not be identical to the cavity shape. For example, a portion of the custom cone can extend above the cavity. Similarly, depending upon the physical properties of the material used to make the custom cone, the size of the cone can be altered. For example, if the custom cone is made from a material that can be deformed, the cone can be shaped slightly larger than the cavity, allowing for compression of the cone when inserted into the cavity. Thus, the surgical system can simulate 320 the cone shape and position based upon the intended use and configuration of the custom cone.

In certain implementations, the surgeon can view the shape and position of the custom cone on the touchscreen as described above. Depending upon the surgeon's preferences, or upon specific circumstances related to the specific surgical procedure being performed, the surgeon can choose to alter the size or position of the custom cone as simulated by the surgical system. The surgical system can adjust the simulated cone shape and position in response to the surgeon's alterations and simulate 320 an updated custom cone shape and position. The surgeon can further be prompted to approve the updated custom cone shape and position or to provide additional alterations.

The surgical system can create 325 a set of instructions for machining the custom cone. Based upon the instructions, the custom cone can be machined 330. Additional details related to creating instructions for machining the custom cone and the actual machining of the custom cone are described in the discussion of FIGS. 4-6 below.

After the custom cone has been machined 330, the surgeon can trial fit 335 the custom cone in the implant cavity. The surgeon can analyze the fit of the custom cone and determine 340 whether the implant will be stable following the revision surgery. If the surgeon determines 340 that stability has been achieved, the surgeon can proceed to install 345 the cone and the implant component and continue the revision surgery. Conversely, if the surgeon determines 340 that stability has not been achieved, the surgeon can use the surgical system to update the design of the custom cone. In response to the updated design, the surgical system can update 350 the machining instructions and the previously made custom cone can be further machined or a new custom cone can be machined 330.

In certain implementations, machine clearance and mating conditions can be analyzed for the custom cone to fit a preferred size and position of the implant components being used. For example, the size and type of implant component being used, as well as other features of the implant component (e.g., the internal geometry, anterior femoral flange, tibial fins, and hemi-augments), can be analyzed to determine the clearance and mating conditions for the custom cone. For example, International Publication No. WO 2016/183446 entitled "Anatomically Shaped Augments," the content of which is incorporated herein by reference, teaches augments that have a shape configured to generally conform to the shape of the cavity where the augment and associated implant are to be inserted.

Thus, in some examples, a revision procedure can include determining size and position information for all custom cones for all relative implant components for each bone. For example, tibial determination can be performed early in a procedure, while femoral determination can be performed to account for any balancing/positioning needs that arise from the placement of the tibia implant. For example, such a determination can occur prior to creating 325 the instructions for machining the implant.

Additionally, in some embodiments, a strength analysis and feasibility analysis can be performed to analyze the strength of the custom cone based upon a combination of a variable internal geometry and a variable external geometry for the custom cone. Such an analysis can be performed, for example, prior to simulating 320 the custom cone.

Figure 4:
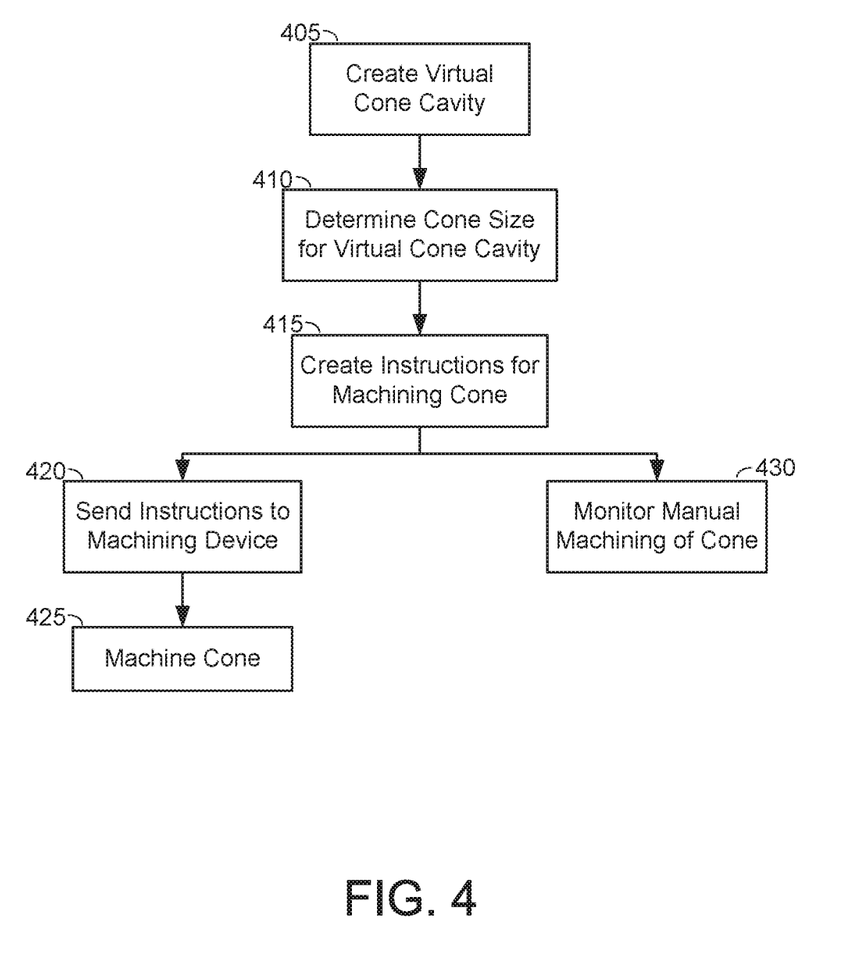
FIG. 4 depicts a sample flow diagram of creating a patient-specific cone in accordance with an embodiment.

FIG. 4 illustrates a sample process for machining the custom cone as described in the discussion of FIG. 3. Similar to FIG. 3, the surgical system can create 405 the virtual cone cavity based upon information received from the tracking system. The surgical system can determine 410 the custom cone size and shape based upon the virtual cone cavity.

Based upon the determined 410 size and shape, the surgical system can create 415 the tool path and/or instructions for machining the custom cone. Depending upon the type of process used for the machining of the custom cone, creation 415 of the tool path and/or instructions can vary accordingly.

For example, if the custom cone is going to be machined by a specialized milling or cutting machine, the surgical system can create a set of instructions and/or a 3D representation of the cone to be created per the input requirements of the cutting machine. For example, if the cutting machine is a CNC machine, the surgical system can create a 3D model file including a representation of the custom cone to be created. The 3D file can be saved as, for example, a .DWG, .DXF, .DGN, .STL, or another similar model file. The surgical system can send 420 the file/instructions to the cutting machine and, based upon the model file, the cutting machine can machine 425 the custom cone using traditional cutting techniques.

In another implementation, the surgeon can use a computer-assisted cutting tool, such as a rotary cutting tool, to machine the custom cone from a cone blank. In such an implementation, the surgical system can monitor 430 the manual cutting of the custom cone and, when appropriate, adjust the operation of the cutting device. Additional detail related to a surgeon manually creating the custom cone is provided in the following discussion of FIGS. 5A, 5B, and 6.

Figure 5A:
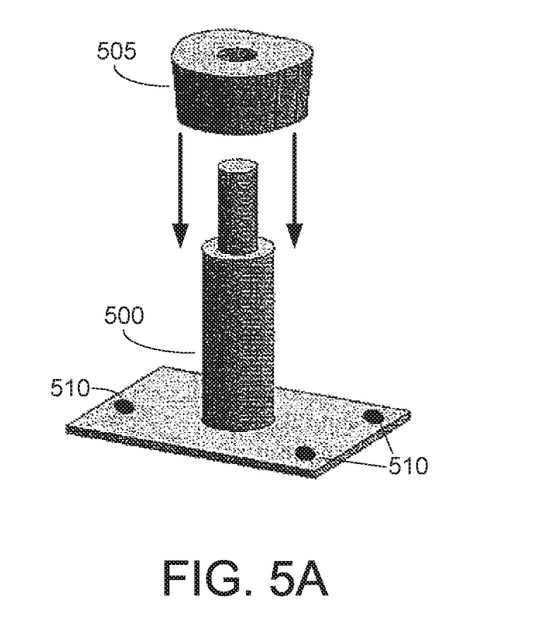
FIGS. 5A and 5B depict a cone blank and shaping fixture for use in creating a patient-specific cone in accordance with an embodiment.

FIG. 5A illustrates a shaping fixture 500 that can be used intraoperatively for manually shaping a patient-specific custom cone. As shown in FIG. 5A, a cone blank 505 can be affixed to the shaping fixture 500. As noted above, each cone can be custom sized and shaped for each patient. As such, each cone blank 505 can have the same initial dimensions prior to any cutting or machining. Thus, when the cone blank 505 is affixed to the shaping fixture 500, a tracking and navigation system can determine the outer dimensions of the cone blank 505 relative to the shaping fixture 500.

Figure 5B:
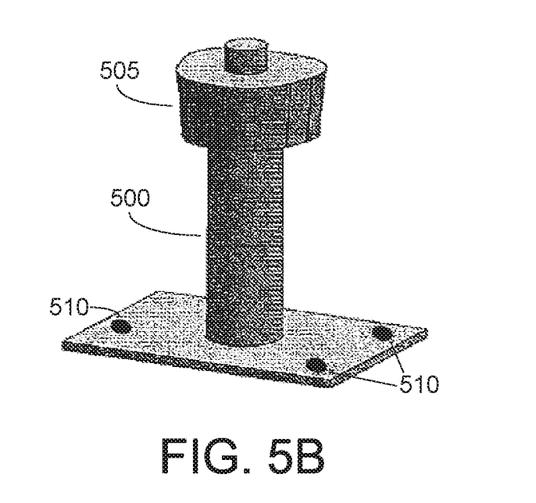

For example, the shaping fixture 500 can include a series of registration points 510. The surgeon can use a probe or other similar pointing device to register the shaping fixture 500 with the tracking system by selecting each of the registration points 510 with, for example, a tracked probe. The tracking system can use the spatial information of the shaping fixture 500 and the dimensional information of the cone blank 505 to provide operational instructions to a cutting device, such as a handheld rotary cutting tool. For example, as shown in FIG. 5B, once the cone blank 505 is affixed to the shaping fixture 500, the surgeon can use a tracked handheld cutting tool to begin shaping a custom cone for the patient. As the tracking system, in combination with the navigation and control systems (of the computer-aided robotic surgical system), tracks the position of the cutting tool the control system can control the operation of the cutting tool to ensure that the cutting tool only removes appropriate material from the cone blank 505 resulting in creation of the custom cone.

As noted above in the discussion of FIG. 3, the computer-aided robotic surgical system can simulate a cone shape and size when creating the custom cone. From this information, the surgical system can create a minimum cone volume that the custom cone should have to fit the patient. In order to accurately provide instructions and control signals to the cutting device to create the custom cone, the surgical system can insert or overlay this minimum cone value into or on a virtual representation of the cone blank to create the cutting instructions.

Figure 6:
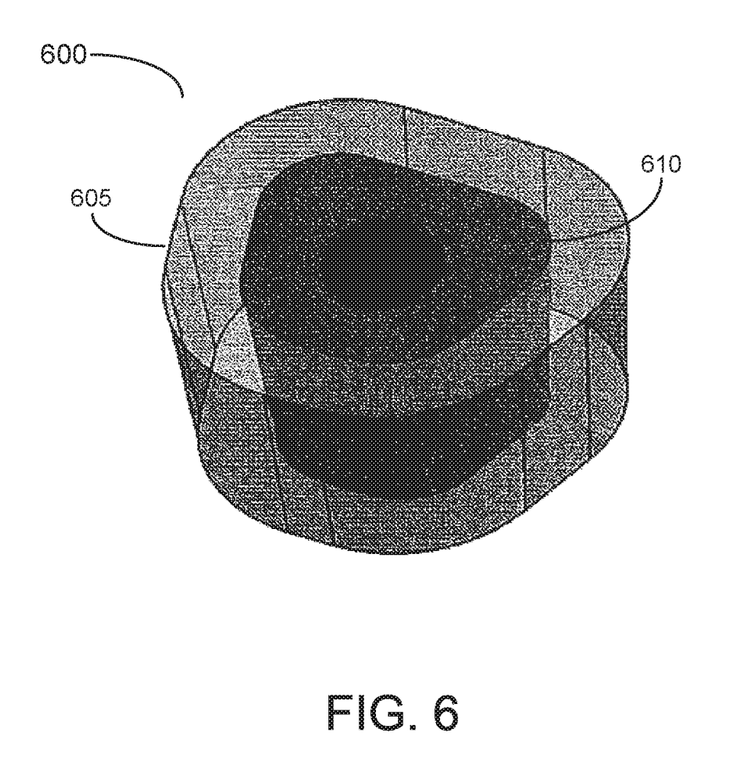
FIG. 6 depicts a virtual mapping for creating a patient-specific cone in accordance with an embodiment.

For example, as shown in FIG. 6, a digital representation of the cone blank 600 can be created. The cone blank 600 can include an area of cone material to be removed 605 and a minimum cone volume 610 for the custom cone. Thus, when determining cutting instructions, the surgical system can instruct a cutting device to remove the removable cone material 605 by tracking the cutting device (e.g., while the cone blank is mounted on a shaping fixture, such as shaping fixture 500 shown in FIGS. 5A and 5B) and providing power to the cutting device while the cutting surface of the cutting device is within the cone material to be removed 605. For example, the rotary tool can be tracked and the burr tip can be spun and extended or retracted based upon its position in relation to the minimum cone volume 610. In such an example, the surgeon can simply trace the surface of the cone blank 600 as the cutting device accurately and automatically removes the cone material 605, leaving the minimum volume 610 for the custom cone uncut and ready for insertion into the patient.

In some implementations, the cutting tool for creating the custom cone can be mounted on and/or controlled by a robotic arm. For example, a rotary tool can be mounted to a robotic arm configured to simulate the movement of a human arm. The surgical system can provide instructions to the robotic arm to manipulate the rotary tool to cut the custom cone automatically, thereby reducing or eliminating the interaction the surgeon has with the cutting tool during the custom cone cutting process.

The techniques as described herein provide for improved revision surgeries for joint implants. By creating a custom cone, the fit and stability of the implant components in the revision surgery can be improved, thereby resulting in higher patient satisfaction following the revision surgery and longer times between revision surgeries. However, the techniques as described herein can be used for other surgical techniques, including additional approaches to revision surgery.

For example, rather than machining a custom cone to fit an implant cavity, the automated tracking and tool operation techniques as described herein can be used to assist the surgeon in preparing an implant cavity to receive a prefabricated cone that does not need any intraoperative alteration. Similarly, a semi-custom cone can be created prior to a surgical procedure for a patient based upon imaging data such as X-rays or MRI data. The size of the semi-custom cone can be approximated based on the patient's need during the revision surgery. The surgical system can assist the surgeon in shaping the implant cavity to the appropriate size and shape to receive the semi-custom cone during the revision surgery.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A method of augmenting an implant intraoperatively, the method comprising:
   removing an existing implant from an implant cavity;
   determining a shape of the implant cavity;
   selecting a shape and position for a cone based on at least the determined shape of the implant cavity;
   machining the cone, wherein the machined cone has the shape selected for the cone;
   installing the cone at the selected position within the implant cavity; and
   installing a revision implant in the cone.

2. The method of claim 1, further comprising:
   defining a coordinate system for a tracking and navigation system during a surgical procedure.

3. The method of claim 2, wherein defining a coordinate system comprises identifying a set of fiduciary points on a patient using a registered probe having a plurality of optical trackers.

4. The method of claim 1, wherein determining the shape of the implant cavity comprises tracing a surface of the implant cavity using a registered probe having a plurality of optical trackers.

5. The method of claim 1, wherein determining the shape of the implant cavity comprises tracking a location of a cutting device used to shape the surface of the implant cavity.

6. The method of claim 1, further comprising simulating the shape and position of the cone using a graphical user interface.

7. The method of claim 6, wherein selecting the shape and position of the cone comprises:
   modifying one or more of the shape of the cone and the position of the cone within the graphical user interface; and
   altering the selected shape and position of the cone based on the modifications.

8. The method of claim 1, further comprising creating a set of instructions for machining the cone.

9. The method of claim 1, wherein machining the cone comprises machining the cone intraoperatively.

10. The method of claim 1, further comprising:
    updating the shape of the cone from the selected shape to a revised shape; and
    machining the machined cone to the revised shape.

11. A method of preparing a custom cone for a revision surgical procedure, the method comprising:
    providing a cone blank having a standardized size and shape on a shaping fixture;
    determining, by a tracking and navigation system, outer dimensions for the cone blank based on the standardized size and shape of the cone blank and one or more registration features of the shaping fixture;
    determining, by the tracking and navigation system, a position of a cutting device; and
    providing one or more operational instructions to the cutting device to shape the cone blank to the custom cone.

12. The method of claim 11, further comprising:
    registering the one or more registration features on the shaping fixture by identifying a set of fiduciary points on the shaping fixture using a registered probe having a plurality of optical trackers.

13. The method of any of claim 11, wherein providing one or more operational instructions comprises controlling, by a control system in operable communication with the tracking and navigation system, operation of the cutting device based on the position of the cutting device and the custom cone shape.

14. The method of claim 13, wherein controlling operation of the cutting device comprises wirelessly controlling operation of the cutting device.

15. The method of claim 11, wherein the cutting device is a handheld cutting device.

16. The method of claim 11, wherein the cutting device comprises a plurality of optical trackers.

17. A method of preparing a custom cone for a revision surgical procedure, the method comprising:
    providing a cone blank having a standardized size and shape on a shaping fixture;
    determining a minimum cone volume for the custom cone;
    determining, by a tracking and navigation system, a location of the cone blank;
    determining, by the tracking and navigation system, a location of a cutting device, wherein the cutting device comprises a cutting element; and
    causing the cutting device to operate the cutting element when the cutting element of the cutting device is located within removable cone material surrounding the minimum cone volume of the cone blank.

18. The method of claim 17, wherein determining a minimum cone volume for the custom cone comprises generating a three-dimensional model of the cone blank comprising the minimum cone volume surrounded by the removable cone material.

19. The method of claim 17, wherein determining a minimum cone volume comprises:
    determining a shape of an implant cavity; and
    selecting a shape and position for the minimum cone value based on at least the determined shape of the implant cavity.

20. The method of claim 17, wherein determining a location of the cone blank comprises registering one or more registration features on the shaping fixture by identifying a set of fiduciary points on the shaping fixture using a registered probe having a plurality of optical trackers.

21. The method of claim 17, wherein determining a location of a cutting device comprises identifying a location of each of a plurality of optical trackers associated with the cutting device.

22. A system for augmenting an implant intraoperatively, the system comprising:
    a cutting device having a communication system, a cutting element, and a plurality of optical trackers;
    a tracking and navigation system configured to detect a location of one or more optical trackers;
    a control system in operable communication with the tracking and navigation system and the cutting device, wherein the control system is configured to:
      cause the tracking and navigation system to detect a location of the cutting device by identifying a location of the plurality of optical trackers associated with the cutting device,
      determine a revised shape for an implant cavity,
      cause the cutting device to cut the implant cavity to the revised shape when the tracking and navigation system identifies that the cutting element is positioned within the implant cavity,
      select a shape for a cone based on at least the determined shape of the implant cavity, and
      cause the cutting device to machine a cone blank to the selected shape when the tracking and navigation system identifies that the cutting element is positioned in proximity to the cone blank.

23. The system of claim 22, wherein the communication system of the cutting device comprises a wireless communication system.

24. The system of claim 22, wherein the cutting element of the cutting device comprises a rotary burr.

25. The system of claim 22, further comprising:
    a probe having a plurality of optical trackers; and
    a shaping fixture comprising a plurality of registration points,
    wherein the control system is further configured to determine a location of the shaping fixture by:
    directing a user to place the probe on each of the plurality of registration points, and
    for each registration point, causing the tracking and navigation system to detect a location of the plurality of optical trackers associated with the probe.

* * * * *